(12) United States Patent
Fain et al.

(10) Patent No.: US 7,930,017 B1
(45) Date of Patent: Apr. 19, 2011

(54) METHOD AND SYSTEM FOR TRENDING VARIATION IN CORONARY BURDEN ACROSS MULTIPLE HEART RATE RANGES

(75) Inventors: Eric S. Fain, Menlo Park, CA (US); Jay Snell, Studio City, CA (US); Katie Hoberman, S. Pasadena, CA (US); Laleh Jalali, Moorpark, CA (US); Bing Zhu, Sunnyvale, CA (US); Jeffery D. Snell, Chatsworth, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 523 days.

(21) Appl. No.: 11/753,759

(22) Filed: May 25, 2007

(51) Int. Cl.
*A61B 5/04* (2006.01)

(52) U.S. Cl. .......................... 600/509; 600/515; 607/14

(58) Field of Classification Search .................. 600/508, 600/509, 515; 607/14, 17, 25
See application file for complete search history.

(56) References Cited

U.S. PATENT DOCUMENTS

| | | | |
|---|---|---|---|
| 5,251,621 A | 10/1993 | Collins et al. | |
| 6,016,443 A | 1/2000 | Ekwall | |
| 6,021,350 A | 2/2000 | Mathson | |
| 6,115,628 A | 9/2000 | Stadler et al. | |
| 6,128,526 A | 10/2000 | Stadler et al. | |
| 6,256,538 B1 | 7/2001 | Ekwall | |
| 6,324,421 B1 | 11/2001 | Stadler et al. | |
| 6,609,023 B1 | 8/2003 | Fischell et al. | |
| 6,937,899 B2 | 8/2005 | Sheldon et al. | |
| 2005/0059897 A1 | 3/2005 | Snell et al. | |
| 2005/0113705 A1* | 5/2005 | Fischell et al. | 600/515 |
| 2006/0009811 A1 | 1/2006 | Sheldon et al. | |
| 2006/0116593 A1 | 6/2006 | Zhang et al. | |
| 2006/0167519 A1 | 7/2006 | Gill et al. | |
| 2007/0208263 A1* | 9/2007 | John et al. | 600/509 |

FOREIGN PATENT DOCUMENTS

| | | |
|---|---|---|
| EP | 1164933 B1 | 5/2006 |
| WO | 00/057781 A1 | 10/2000 |
| WO | 03020366 A1 | 3/2003 |
| WO | 03020367 A1 | 3/2003 |
| WO | 2004047917 A1 | 6/2004 |

* cited by examiner

*Primary Examiner* — Carl H Layno
*Assistant Examiner* — Pamela M Bays
(74) *Attorney, Agent, or Firm* — Steven M Mitchell

(57) ABSTRACT

A method and system are provided for trending variation in coronary burden across multiple heart rate ranges. The method and system include obtaining cardiac signals having a segment of interest over a period of time where each cardiac signal has an associated heart rate that falls within at least one heart rate range. Segment variations of the segment of interest are determined and grouped based on the associated heart rates to produce distributions of segment variations that are associated with the heart rate ranges. Trending information is produced by automatically comparing the distributions of segment variations between different heart rate ranges.

23 Claims, 13 Drawing Sheets

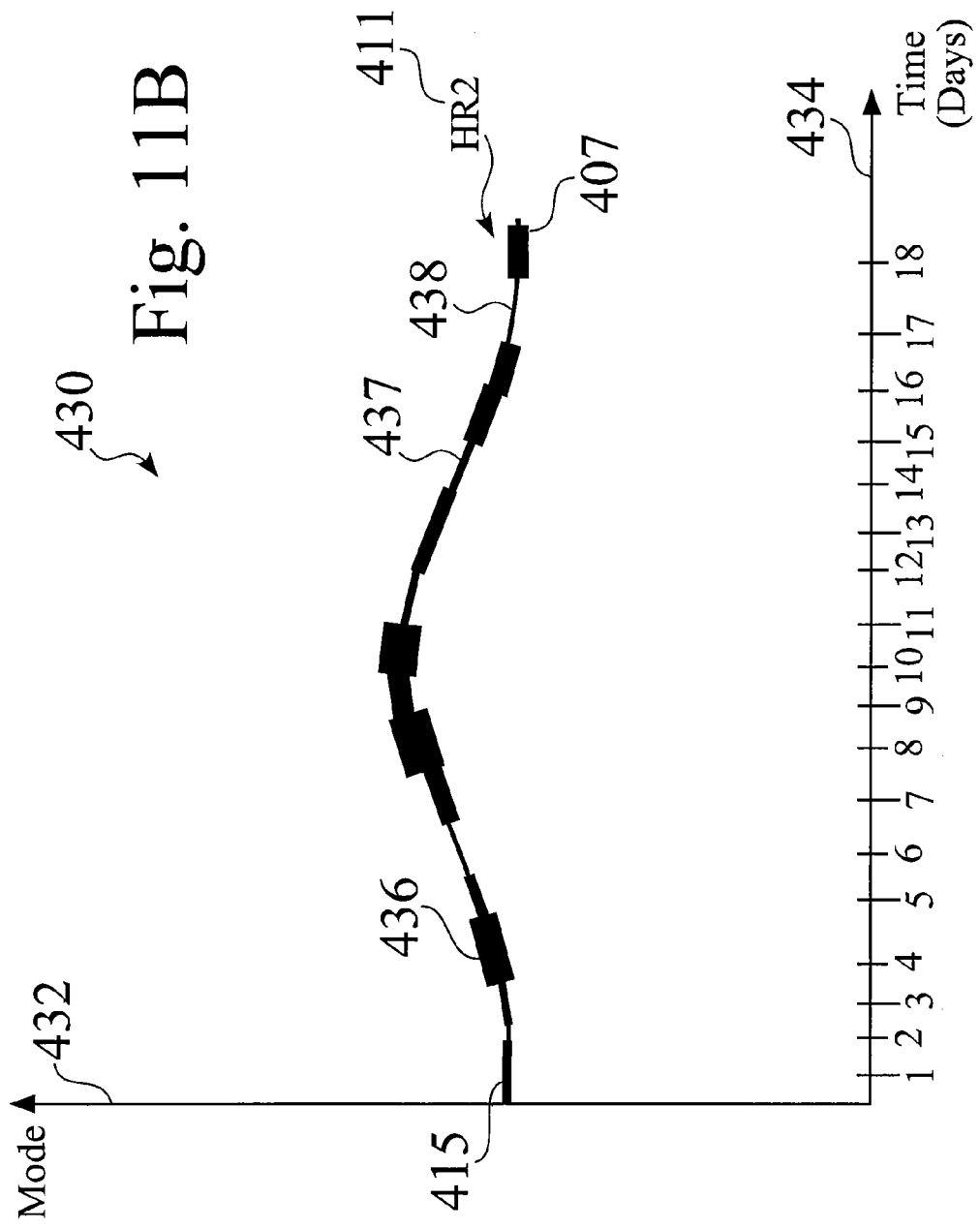

METHOD AND SYSTEM FOR TRENDING VARIATION IN CORONARY BURDEN ACROSS MULTIPLE HEART RATE RANGES

BACKGROUND OF THE INVENTION

Embodiments of the present invention generally relate to implantable medical devices, and more particularly to implantable and external medical devices that utilize segment variations across multiple heart rate ranges to trend coronary burden.

An implantable medical device is implanted in a patient to monitor, among other things, electrical activity of a heart and to deliver appropriate electrical and/or drug therapy, as required. Implantable medical devices ("IMDs") include for example, pacemakers, cardioverters, defibrillators, implantable cardioverter defibrillators ("ICD"), and the like. The electrical therapy produced by an IMD may include, for example, pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. Ischemia and AMI represent related types of acute coronary burden.

Cardiac ischemia is a condition whereby heart tissue does not receive adequate amounts of oxygen and is usually caused by a blockage of an artery leading to heart tissue. Ischemia arises during angina, acute myocardial infarction, coronary angioplasty, and any other condition that compromises blood flow to a region of tissue. Ischemia can occur as a result of increased myocardial oxygen demand, reduced myocardial oxygen supply, or both. In the presence of a coronary obstruction (e.g., blockage of an artery), an increase of myocardial oxygen requirements caused by exercise, tachycardia, and the like leads to a transitory imbalance termed "demand ischemia". Demand ischemia develops in patients with increased demand for cardiac output or perfusion when the myocardial blood supply may be marginal or inadequate. Demand ischemia may be responsible for many episodes of chronic stable angina and usually manifests as a predictable angina that occurs during increased activity. Demand ischemia can be evaluated by means of an exercise stress test and is depicted as a transient depression in the ST segment of the cardiac signal associated with exertion during exercise.

In other situations, an imbalance between the need for myocardial oxygen and the ability to provide myocardial oxygen maybe caused by an acute reduction of oxygen supply (e.g., coronary vasospasm). In addition, the imbalance may be due to a reduction or cessation of coronary blood flow (e.g., within arteries and veins) as a result of platelet aggregates or thrombi, which is termed "supply ischemia". Supply ischemia manifests as angina at rest or during exercise (e.g., Prinzmetal type angina) and is often responsible for myocardial infarction ("MI") and most episodes of unstable angina ("UA"). Unstable angina may result from spontaneous thrombus formation and is not necessarily associated with exercise or stress. The onset of UA is therefore unpredictable and patients having UA should seek medical attention.

Implantable medical devices are utilized today for monitoring cardiac signals and delivering certain therapies based arrhythmias detected from the cardiac signals. In general, IMDs have limited memory space for storing cardiac signals and/or characteristics associated with the cardiac signals. For example, the IMD may store cardiac signals for a limited number of cardiac cycles, such as surrounding an event of interest. The stored cardiac signals are later telemetered from the IMD for analysis.

However, conventional IMDs have not been able to detect or record sufficient information to enable a later analysis and diagnosis of supply or demand type ischemia. For example, IMDs have been proposed with the capability to store information regarding variations in ST segments for a limited number of cardiac cycles. However, conventional IMDs do not store a sufficient amount, nor type, of ST segment related information to facilitate analysis and diagnosis of supply and demand ischemia.

A need remains for an IMD capable of storing information that enables the ability to evaluate if ischemia is present, categorize the type of ischemia as demand ischemia or supply ischemia, and determine the relative frequency in which ischemia occurs over a specified period of time.

SUMMARY

In accordance with at least one embodiment, a method is provided for trending variation in coronary burden across multiple heart rate ranges. The method includes obtaining cardiac signals having a segment of interest over a period of time where each cardiac signal has an associated heart rate that falls within at least one heart rate range. The method then determines segment variations of the segment of interest and groups the segment variations based on the associated heart rates to produce distributions of segment variations that are associated with the heart rate ranges. Trending information is produced by automatically comparing the distributions of segment variations between different heart rate ranges.

Optionally, the method may provide distributions of segment variations that represent histograms. The distributions are produced periodically to provide the ST segment variations over a period of time as the trending information. One of the distributions of segment variations maybe identified as a reference distribution. The reference distribution is compared to at least one other of the distributions of segment variations, such as based on a statistical parameter, to determine a difference between at least one of a mean, mode, variance, average deviation and standard deviation for at least two distributions of segment variations. The method compares histograms, specifically determining a difference in values for a parameter associated with the histograms, across different heart rate ranges to produce a trend over a predetermined period of time. The method graphically presents the trending information.

In accordance with another embodiment, a system for trending variation in coronary burden across multiple heart rate ranges is provided. The system includes an input for obtaining cardiac signals over a period of time. The cardiac signals have a segment of interest and an associated heart rate. The heart rate falls within at least one of the heart rate ranges. The system includes a processor for determining segment variations of the segment of interest within the cardiac signals and a memory to store distributions of the segment variations. The distributions are based on the associated heart rates of the cardiac signals from which the segment variations were determined. The processor produces trending information by comparing the distributions of segment variations between different heart rate ranges.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 illustrates an implantable medical device formed in accordance with an embodiment of the present invention.

FIG. 11B illustrates a graph showing trend data presented over time with an indication of the number of heart beats per unit time in accordance with an embodiment of the present invention.

DETAILED DESCRIPTION

In the following detailed description, reference is made to the accompanying drawings which form a part hereof, and in which is shown by way of illustration specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. For example, embodiments may be used with a pacemaker, a cardioverter, a defibrillator, and the like. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

The term "coronary burden" is used, generally, to include ischemic events, ischemic episodes, AMI events, AMI episodes and the like. The term "segment of interest" is used generally to refer to any combination of two or more adjacent segments within a cardiac cycle, such as the PQ segment, QR segment, RS segment, ST segment, QRS segment, PQR segment, QRST segment, PQRST segment and the like.

Figure 1:
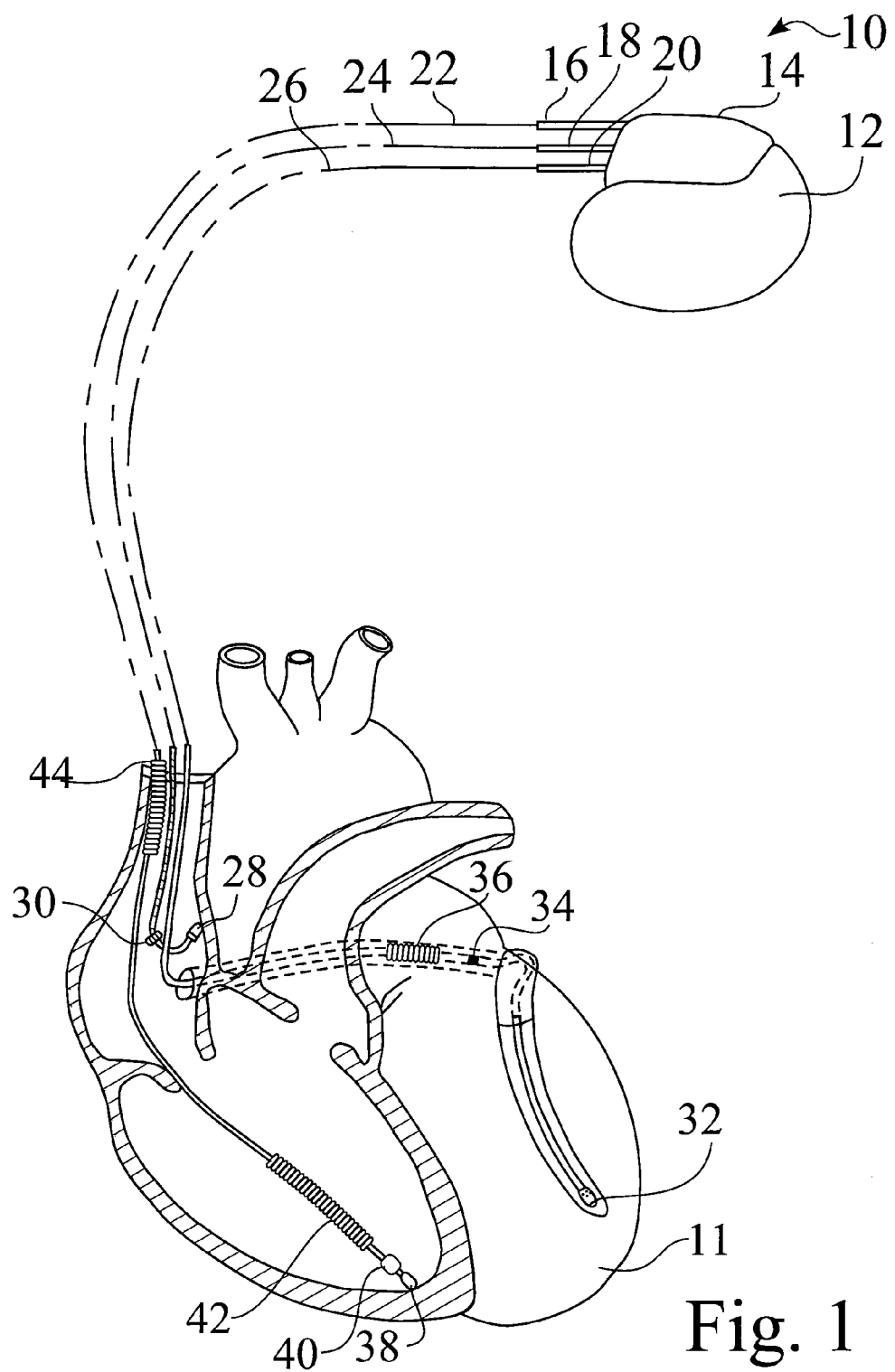

FIG. 1 illustrates an implantable medical device 10 ("IMD") that is coupled to a heart 11. The implantable medical device 10 may be a cardiac pacemaker, an implantable cardioverter defibrillator ("ICD"), a defibrillator, or an ICD coupled with a pacemaker implemented in accordance with an embodiment of the present invention. The IMD 10 may be a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto. As explained below in more detail, the IMD 10 may be controlled to monitor cardiac signals and based thereof, to identify potentially abnormal physiology (e.g., ischemia). The detected cardiac signals may include intrinsic heart beats that have no assistance from any type of manmade electrical stimulation. Alternatively, the detected cardiac signals may include heart beats that have been stimulated by an electrical source to produce a paced heartbeat. The electrical source that provides the paced heartbeat may include an implantable device that provides low energy electrical signals, such as provided by a pacemaker, a demand pacemaker, a single-chamber pacemaker, a dual chamber pacemaker, a biventricular pacemakers and the like. Optionally, the paced heartbeat may be generated by an implantable device that provides high energy electrical signals such as those provided by an implantable cardioverter defibrillator.

The IMD 10 includes a housing 12 that is joined to a header assembly 14 (e.g., an IS-4 connector assembly) that holds receptacle connectors 16, 18, and 20 that are connected to a right ventricular lead 22, a right atrial lead 24, and a coronary sinus lead 26, respectively. The leads 22, 24 and 26 may be located at various locations, such as an atrium, a ventricle, or both to measure the physiological condition of the heart 11. One or more of the leads 22, 24 and 26 detect intra-cardiac electrogram ("IEGM") signals that form an electrical activity indicator of myocardial function over multiple cardiac cycles. To sense atrial cardiac signals and to provide right atrial chamber stimulation therapy, the right atrial lead 24 having at least an atrial tip electrode 28, which is typically implanted in the right atrial appendage, and an atrial ring electrode 30. The IEGM signals represent analog cardiac signals that are subsequently digitized and analyzed to identify waveforms of interest. Examples of waveforms identified from the IEGM signals include the P-wave, T-wave, the R-wave, the QRS complex and the like. The waveforms of interest may be collected over a period of time, either continuously or at defined intervals.

The coronary sinus lead 26 receives atrial and ventricular cardiac signals and delivers left ventricular pacing therapy using at least a left ventricular tip electrode 32, left atrial pacing therapy using at least a left atrial ring electrode 34, and shocking therapy using at least a left atrial coil electrode 36. The right ventricular lead 22 has a right ventricular tip electrode 38, a right ventricular ring electrode 40, a right ventricular ("RV") coil electrode 42, and a SVC coil electrode 44. Therefore, the right ventricular lead 22 is capable of receiving cardiac signals, and delivering stimulation in the form of pacing and shock therapy to the right ventricle.

Figure 2:
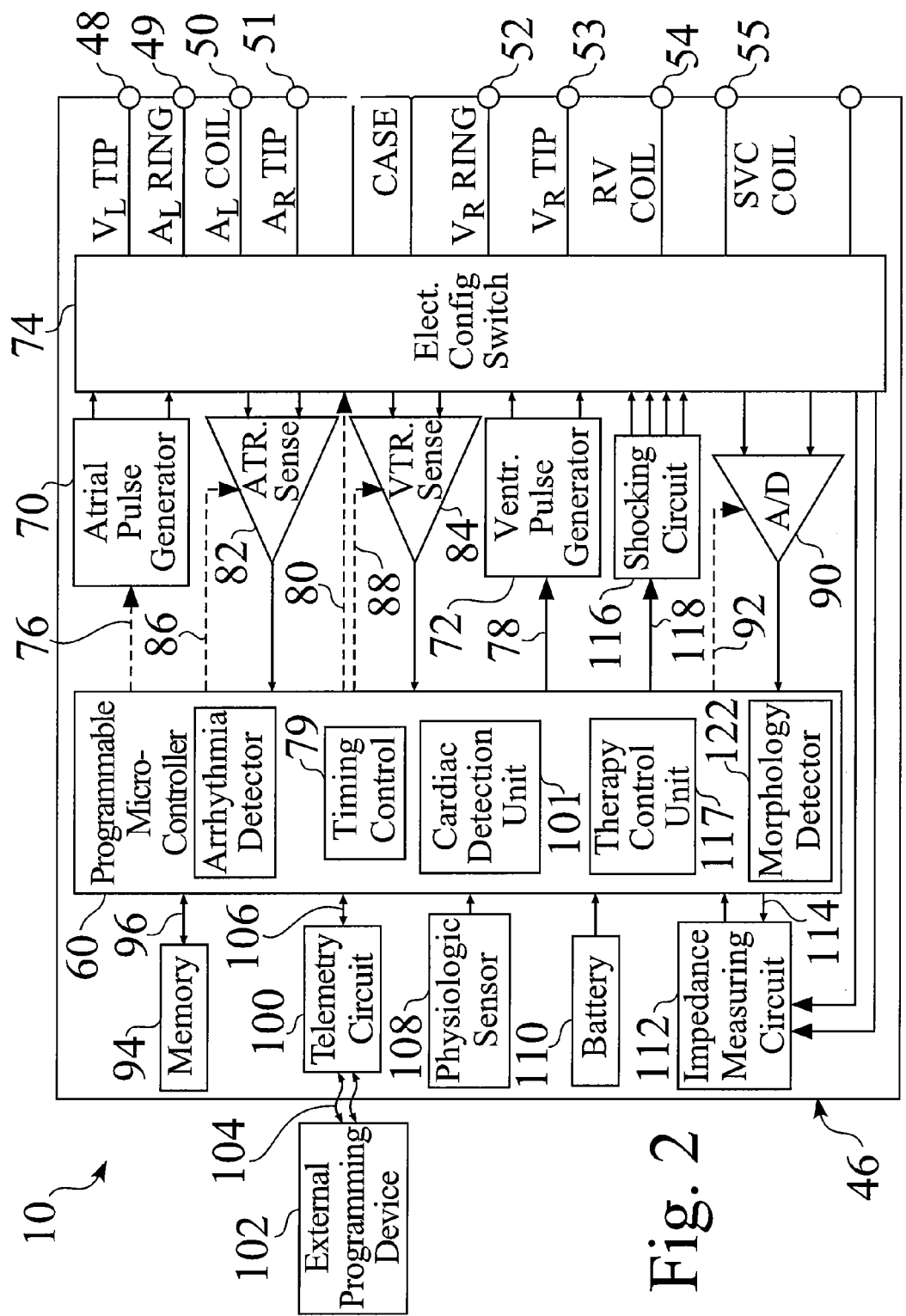
FIG. 2 illustrates a functional block diagram of exemplary internal components of an implantable medical device formed in accordance with an embodiment of the present invention.

FIG. 2 illustrates a block diagram of exemplary internal components of the IMD 10. The IMD 10 is for illustration purposes only, and it is understood that the circuitry could be duplicated, eliminated or disabled in any desired combination to provide a device capable of treating the appropriate chamber(s) of the heart with cardioversion, defibrillation and/or pacing stimulation.

The housing 46 for IMD 10 (shown schematically in FIG. 2), is often referred to as the "can", "case" or "case electrode" and may be programmably selected to act as the return electrode for all "unipolar" modes. The housing 46 further includes a connector (not shown) having a plurality of terminals, namely a right atrial tip terminal ($A_R$ TIP) 51, a left ventricular tip terminal ($V_L$ TIP) 48, a left atrial ring terminal ($A_L$ RING) 49, a left atrial shocking terminal ($A_L$ COIL) 50, a right ventricular tip terminal ($V_R$ TIP) 53, a right ventricular ring terminal ($V_R$ RING) 52, a right ventricular shocking terminal ($R_V$ COIL) 54, and an SVC shocking terminal (SVC COIL) 55.

The IMD 10 includes a programmable microcontroller 60, which controls the operation of the IMD 10 based on acquired cardiac signals. For example, the microcontroller 60 includes a cardiac detection unit 101 to monitor the cardiac signals and to identify therein ST segment shifts and determine potential ischemic and AMI conditions. The microcontroller 60 (also referred to herein as a processor module or processor unit) typically includes a microprocessor, or equivalent control circuitry, is designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in memory.

Among other things, the microcontroller 60 receives, processes, and manages storage of digitized data from the various electrodes. The microcontroller 60 may also analyze the data, for example, in connection with collecting, over a period of time, reference ST segment variations in a cardiac signal (e.g., sense signals received from leads 22, 24 and 26). The microcontroller 60 may obtain a ST threshold by statistically determining variability in the ST segment shift based on reference ST segment shifts. The microcontroller 60 may also measure ST segment shifts and compare them to the ST threshold to identify a potential abnormal physiology (e.g., such as when the patient is having a post-myocardial infarct, a "silent" myocardial infarct, a myocardial infarct, an ischemia, a heart block, an arrhythmia, fibrillation, congestive heart failure, and the like).

The microcontroller 60 trends variation in coronary burden across multiple heart ranges. For example, microcontroller 60 determines segment variations (e.g., ST segment variation) of a segment of interest within a cardiac signal and stores the segment variations in memory 94. Microcontroller 60 determines distributions of the segment variations where the distributions are based on an associated heart rate of the cardiac signal from which the segment variations were determined. The microcontroller 60 then compares the distributions of segment variations between different heart rate ranges, over a predetermined period of time. The differences between the distributions define trending information. For instance, the microcontroller 60 may identify a relation between a first series of distributions associated with a first heart rate range and a second series of distributions associated with a second heart rate range. The relation may be the difference between first and second values for a statistical parameter, such as a mean, a mode, a variance, an average deviation, a standard deviation, and the like. Further, when the distributions are stored in memory 94 as histograms, microcontroller 60 may determine the differences between various histograms of heart rate ranges over a predetermined period of time.

The IMD 10 includes an atrial pulse generator 70 and a ventricular/impedance pulse generator 72 to generate pacing stimulation pulses. In order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

Switch 74 includes a plurality of switches for connecting the desired electrodes to the appropriate I/O circuits, thereby providing complete electrode programmability. Atrial sensing circuits 82 and ventricular sensing circuits 84 may also be selectively coupled to the leads through the switch 74 for detecting the presence of cardiac activity in each of the four chambers of the heart. Control signals 86 and 88 from processor 60 direct output of the atrial and ventricular sensing circuits, 82 and 84, that are connected to the microcontroller 60. In this manner, the atrial and ventricular sensing circuits, 82 and 84 are able to trigger or inhibit the atrial and ventricular pulse generators, 70 and 72.

The cardiac signals are applied to the inputs of an analog-to-digital ("A/D") data acquisition system 90. The data acquisition system 90 is configured to acquire IEGM signals, convert the raw analog data into a digital IEGM signals, and store the digital IEGM signals in memory 94 for later processing and/or telemetric transmission to an external device 102. Control signal 92 from processor 60 determines when the data acquisition system 90 acquires signals, stores them in memory 94, or transmits data to an external device 102. The data acquisition system 90 is coupled to the right atrial lead 24, the coronary sinus lead 26, and the right ventricular lead 22 through the switch 74 to sample cardiac signals across any combination of desired electrodes.

The cardiac detection unit 101 receives the cardiac signals from data acquisition system 90 and determines the onset and termination of an ischemic or AMI condition based on ST segment shifts. The ST segment may include variations of ST segments that occur over a period of time. The onset of ischemia may be determined by the cardiac detection unit 101 by using a statistical determination of the variability of the ST segment variation shift. For example, a plurality of ST segment shifts may be collected to obtain a ST threshold. Then the ST threshold is used in a comparison with subsequently measured ST segment shifts to identify the onset of a coronary episode (e.g., demand ischemia or supply ischemia). Upon detecting the onset of a coronary episode, either an ischemic event or an AMI event, the cardiac signals (e.g., IEGM or EGM) are stored in memory 94.

The microcontroller 60 is coupled to the memory 94 by a suitable data/address bus 96, wherein the programmable operating parameters used by the microcontroller 60 are stored and modified, as required, in order to customize the operation of IMD 10 to suit the needs of a particular patient. The memory 94 may also store data indicative of myocardial function, such as the IEGM data, ST segment shifts, ST segment deviations, reference ST segment shifts, and ST segment shift thresholds and the like for a desired period of time (e.g., one hour, 24 hours, a week, two weeks, one month, six weeks, and the like). In addition, the memory 94 may store data for each time a shift of the ST segment is detected that exceeds a predetermined threshold.

Memory 94 may also store large amounts of data in order to determine an ischemic burden, an AMI burden and to determine trends. Each occurrence of an ischemic event or AMI condition that occurs in a patient over a year period of time may be stored in memory 94. In addition, the cardiac signals are categorized according to their heart rate in beats per minute (bpm) and placed in heart rate bins for additional processing. Therefore, the categorization of each cardiac signal may be also stored in memory 94. Furthermore, memory 94 may store statistical parameters based on ST segment shifts (e.g., an average, a mean, a mode, a variance, an average deviation, a standard deviation, and the like). Thus, memory 94 may store all the information necessary to present a series of distributions, on which to base trend information to a user. Memory 94 may store the distributions of segment variations as histograms, where each of the histograms is associated a different heart rate range. For example, memory 94 stores a first series of distributions associated with a first heart rate range over a predetermined period of time and store a second series of distributions associate with a second heart rate range over a predetermined period of time, and the like. The first and second series of distributions are characterized by statistical parameters that are stored in memory 94. The memory 94 may also store instructions that direct the microcontroller 60 to analyze the data to detect ischemia and/or to identify events of interest.

The operating parameters of the IMD 10 may be non-invasively programmed into the memory 94 through a telemetry circuit 100 in communication with the external device 102, such as a programmer (shown in FIG. 3), trans-telephonic transceiver or a diagnostic system analyzer. The telemetry circuit 100 is activated by the microcontroller 60 by a control signal 106. The telemetry circuit 100 allows intracardiac electrograms, and status information relating to the operation of IMD 10 (as contained in the microcontroller 60 or memory 94) to be sent to the external device 102 through an established communication link 104.

The IMD 10 additionally includes a battery 110, which provides operating power to all of the circuits shown within the housing 46, including the processor 60. The IMD 10 is shown as having an impedance measuring circuit 112 which is enabled by the microcontroller 60 via a control signal 114. The impedance measuring circuit 112 is advantageously coupled to the switch 74 so that impedance at any desired electrode may be obtained.

In the case where IMD 10 is intended to operate as an implantable cardioverter/defibrillator ("ISCD") device, the IMD 10 detects the occurrence of an ST segment shift that indicates an arrhythmia, and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (e.g., up to 0.5 joules), moderate (e.g., 0.5-10 joules) or high energy (e.g., 11 to 40 joules), as controlled by the microcontroller 60. Such shocking pulses are applied to the heart 11 of the patient through at least two shocking electrodes, and as shown in this embodiment, selected from the left atrial coil electrode 36, the RV coil electrode 42, and/or the SVC coil electrode 44.

Figure 3:
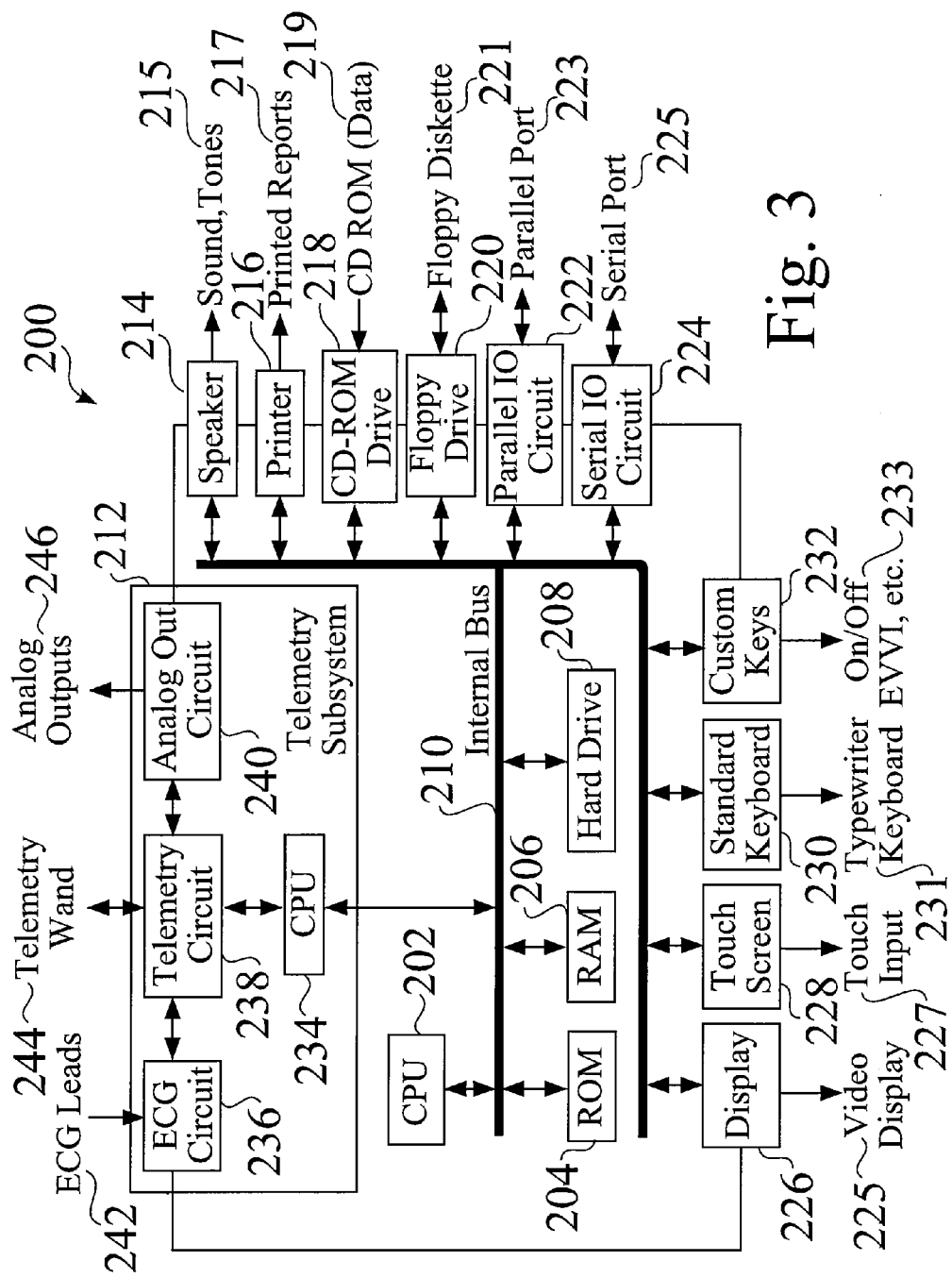
FIG. 3 illustrates a functional block diagram of certain components of an external programmer used to communicate with the implantable medical device shown in FIG. 1 utilized in accordance with an embodiment of the present invention.

FIG. 3 illustrates a functional block diagram of an external device 200, such as a programmer, that is operated by a physician, a health care worker, or a patient to interface with IMD 10. The external device 200 may be utilized in a hospital setting, a physician's office, or even the patient's home to communicate with the IMD 10 to change a variety of operational parameters regarding the therapy provided by the IMD 10, as well as to select among physiological parameters to be monitored and recorded by the IMD 10. Further, the external device 200 may be utilized to interrogate the IMD 10 to determine the condition of a patient, to adjust the physiological parameters monitored, to adjust the heart rate ranges, to adjust the segment of interest, to adjust the period of time for which distributions are collected, or to download cardiac signals, segment variations, distributions of segment variations, trending information, histograms, and the like.

External device 200 includes an internal bus 210 that connects/interfaces with a Central Processing Unit ("CPU") 202, ROM 204, RAM 206, a hard drive 208, a speaker 214, a printer 216, a CD-ROM drive 218, a floppy drive 220, a parallel I/O circuit 222, a serial I/O circuit 224, a display 226, a touch screen 228, a standard keyboard connection 230, custom keys 232, and a telemetry subsystem 212. The internal bus 210 is an address/data bus that transfers information (e.g., either memory data or a memory address from which data will be either stored or retrieved) between the various components described. The hard drive 208 may store operational programs as well as data, such as reference ST segments, ST thresholds, timing information and the like.

The CPU 202 typically includes a microprocessor, a micro-controller, or equivalent control circuitry, designed specifically for controlling interfacing the external device 200 with the IMD 10. The CPU 202 may further include RAM or ROM memory, logic and timing circuitry, state machine circuitry, and I/O circuitry to interface with the IMD 10. Typically, the microcontroller 60 includes the ability to process or monitor input signals (data) as controlled by program code stored in memory (e.g., ROM 204).

In order for a physician or health care worker to communicate with the external device 200, a display 226, a touch screen 228, a standard keyboard 230, and custom keys 232 are provided. The display 226 (e.g., may be connected to a video display 225) and the touch screen 228 display text, alphanumeric information, data and graphic information via a series of menu choices to be selected by the user relating to the IMD 10, such as for example, status information, operating parameters, therapy parameters, patient status, access settings, software programming version, ST segment thresholds, and the like. The display 226 may present trending information over time, such as shown in FIGS. 6-11A. For instance, display 226 may present graphical illustrations of trending information over a predetermined time period. The touch screen 228 accepts a user's touch input 227 when selections are made. The keyboard 230 (e.g., a typewriter keyboard 231) allows the user to enter data as well as interface with the telemetry subsystem 212.

Furthermore, custom keys 232 turn on/off 233 the external device 200, a printer 216 prints hard-copies of any reports 217 for a physician/healthcare worker to review or to be placed in a patient file, and speaker 214 provides an audible warning (e.g., sounds and tones 215) to the user in the event any abnormal situations occur while the external device 200 is being used. In addition, the external device 200 includes a parallel I/O circuit 222 to interface with a parallel port 223, a serial I/O circuit 224 to interface with a serial port 225, a floppy drive 220 to accept floppy diskettes 221, and a CD-ROM drive 218 that accepts CD ROMs 219.

The telemetry subsystem 212 includes a central processing unit (CPU) 234 in electrical communication with a telemetry circuit 238, which communicates with both an ECG circuit 236 and an analog out circuit 240. The ECG circuit 236 is connected to ECG leads 242, the telemetry circuit 238 is connected to a telemetry wand 244, and the analog out circuit 240 includes communication circuits, such as a transmitting antenna, modulation and demodulation stages (not shown), as well as transmitting and receiving stages (not shown) to communicate with analog outputs 246. The external device 200 may wirelessly communicate with the IMD 10 and utilize protocols, such as Bluetooth, GSM, infrared wireless LANs, HIPERLAN, 3G, satellite, as well as circuit and packet data protocols, and the like. The wireless RF link utilizes a carrier signal that is selected to be safe for physiologic transmission through a human being and is below the frequencies associated with wireless radio frequency transmission. Alternatively, a hard-wired connection may be used to connect the external device 200 to IMD 10 (e.g., an electrical cable having a USB connection).

Figure 4:
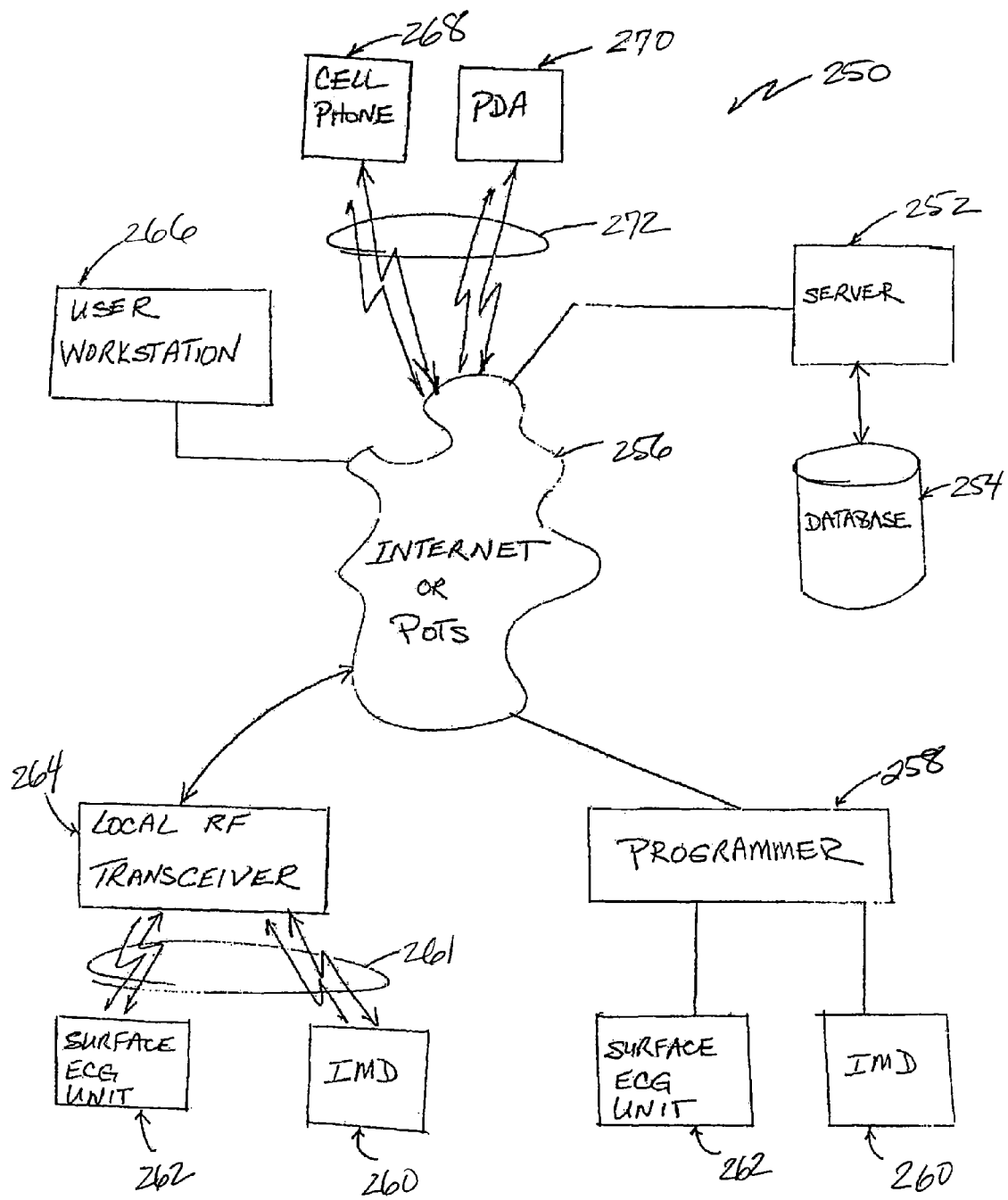
FIG. 4 illustrates a functional block diagram of a distributed processing system utilized in accordance with an embodiment of the present invention.

FIG. 4 illustrates a distributed processing system 250 in accordance with an embodiment of the invention. The distributed processing system 250 includes a server 252 that is connected to a database 254, a programmer 258 (e.g., similar to external device 200 described above), a local RF transceiver 264 and a user workstation 266 electrically connected to a communication system 256 such as the internet, a voice over IP ("VoIP") gateway, or a local plain old telephone service ("POTS") such as a public switched telephone network ("PSTN"). Alternatively, the communication system 256 may be a local area network ("LAN"), a campus area network ("CAN"), a metropolitan area network ("MAN"), or a wide area network ("WAM"). The communication system 256 serves to provide a network that facilitates the transfer/receipt of cardiac signals, processed cardiac signals, segment variations, distributions, histograms, trend analysis and patient status, and the like.

The server 252 is a computer system that provides services to other computing systems (e.g., clients) over a computer network. The server 252 acts to control the transmission and reception of information (e.g., cardiac signals, processed cardiac signals, ST segments, histograms, statistical analysis, trend lines, and the like). The server 252 interfaces with a communication system 256, such as the internet or a local POTS based telephone system, to transfer information between the programmer 258, the local RF transceiver 264, the user workstation 266, as well as a cell phone 268, and a personal data assistant ("PDA") 270 to the database 254 for storage/retrieval of records of information. For instance, the server 252 may download to a cell phone 268 or PDA 270 the results of processed cardiac signals, ST segment trends, or a patient's physiological state (e.g., is the patient having or has had an ischemia) based on previously recorded cardiac information. ST segment trends may include variations of ST segments occurring over a period of time. On the other hand, the server 252 may upload raw cardiac signals (e.g., unprocessed cardiac data) from surface ECG unit 262 or IMD 260 via the local RF transceiver 264 or the programmer 258.

Database 254 is any commercially available database that stores information in a record format in electronic memory. The database 254 stores information such as raw cardiac data, processed cardiac signals, statistical calculations (e.g., averages, modes, average deviations, standard deviations and the like), histograms, coronary burden information, cardiac trends (e.g., ST segment trends), and the like. The information is downloaded into the database 254 via the server 252 or, alternatively, the information is uploaded to the server from the database 254.

The programmer 258 is similar to the programmer 200 described above and may reside in a patient's home, a hospital, or a physician's office. Programmer 258 interfaces with a surface ECG unit 262 and an IMD 260 (e.g., similar to ICD 10 described above). The programmer 258 may wirelessly communicate with the IMD 260 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 258 to IMD 10, e.g., an electrical cable having a USB connection. The programmer 258 is able to acquire cardiac signals from the surface of a person (e.g., ECGs), or the programmer 258 is able to acquire intra-cardiac electrograms (e.g., IEGMs) from IMD 260. The programmer 258 interfaces with the communication system 256, either via the internet or via POTS, to upload the cardiac data acquired from the surface ECG unit 262 or the IMD 260 to the server 252. The programmer 258 may upload more than just raw cardiac data. For instance, the programmer 258 may upload status information, operating parameters, therapy parameters, patient status, preference settings, software programming version, ST segment thresholds, and the like.

The local RF transceiver 264 interfaces with the communication system 256, either via the internet or via POTS, to upload cardiac data acquired from the surface ECG unit 262 or the IMD 260 to the server 252. In one embodiment, the surface ECG unit 262 and the IMD 260 have a bi-directional connection with the local RF transceiver via a wireless connection 261. The local RF transceiver 264 is able to acquire cardiac signals from the surface of a person (e.g., ECGs), or acquire intra-cardiac electrogram (e.g., IEGM) from IMD 260. On the other hand, the local RF transceiver 264 may download stored cardiac data from database 254 or the analysis of cardiac signals from database 254 (e.g., ST segment statistical analysis, ST segment trends, and the like) information to the surface ECG unit 262 or IMD 260.

The user workstation 266 may interface with the communication system 256 via the internet or POTS to download information via the server 252 from the database 254. Alternatively, the user workstation 266 may download raw data from the surface ECG unit 262 or IMD 260 via either the programmer 258 or the local RF transceiver 264. Once the user workstation 266 has downloaded the cardiac information (e.g., raw cardiac signals, ST segments, and the like), the user workstation 266 may process the cardiac signals, create histograms, calculate statistical parameters, or determine cardiac trends and determine if the patient is suffering from ischemia or another physiological condition. Once the user workstation 266 has finished performing its calculations, the user workstation 266 may either download the results to the cell phone 268, the PDA 270, the local RF transceiver 264, the programmer 258, or to the server 252 to be stored on the database 254. Both programmer 258 and workstation 266 may present coronary burden information to illustrate trends.

Figure 5:
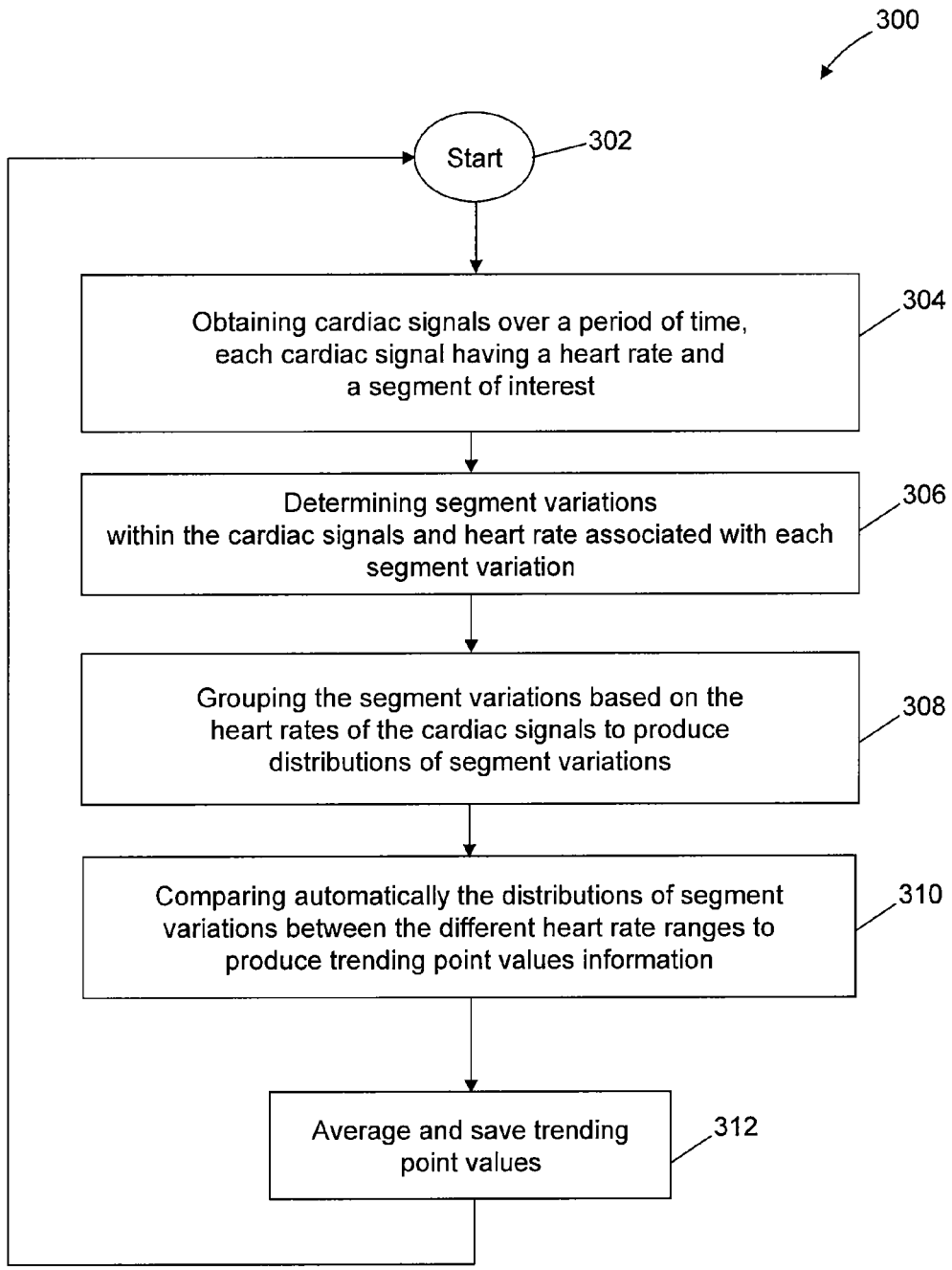
FIG. 5 illustrates a flow chart for trending variation in coronary burden across multiple heart rate ranges presented in accordance with an embodiment of the present invention.

FIG. 5 illustrates a flowchart 300 that depicts a process for trending variation in coronary burden across multiple heart rate ranges in accordance with an embodiment of the present invention. At 302 the process begins.

At 304, the process 300 obtains cardiac signals over a period of time (e.g., a series of cardiac cycles occurring over 10 minutes, 30 minutes, 60 minutes, etc.). The cardiac signals may represent intra-cardiac electrogram ("IEGM") signals, electrocardiogram ("ECG") signals and the like. Furthermore, the cardiac signals may be raw cardiac signals (e.g., ECGs or IEGMs), processed cardiac signals (e.g., ST segment shifts, ST segment variations, ST segment deviations), and the like. Each cardiac signal includes a segment of interest. The segment of interest includes a part, several parts, or the whole cardiac cycle. For instance, the segment of interest may refer, generally, to any combination of two or more adjacent segments within a cardiac cycle, such as the PQ segment, QR segment, RS segment, ST segment, QRS segment, PQR segment, QRST segment, PQRST segment and the like.

Further, each cardiac signal has an associated heart rate, which will depend on whether the patient is active or sedentary. If a patient is sedentary (e.g., sitting, standing, laying down, motionless, and the like) the heart rate will be low (e.g., 40-75 beats per minute). As the patient begins to move about (e.g., walk, jog, run and the like) the heart rate will increase (e.g., greater than 80 bpm). The heart rate will also depend upon whether the patient suffers from a condition that compromises blood flow (e.g., ischemia, demand ischemia, coronary vasospasm, supply ischemia, angina at rest or during exercise, Prinzmetal type angina, myocardial infarction (Ml), unstable angina (UA) and the like). A patient suffering from any condition that compromises blood flow may have an increased heart rate beyond the normal ranges both at rest and during activity.

At 306, segment variations of a particular segment of interest within the cardiac signals are determined. The segment variations may represent ST segment variations over a series of cardiac cycles spanning 30 minutes, one hour and the like. The ST segment may have a voltage level that aligns with the voltage level of a baseline heart rhythm. Alternatively, the ST segment may have a voltage level that is shifted above or shifted below the baseline. The ST segment variation for a particular cardiac cycle represents one of a ST segment shift and a ST segment deviation.

A ST segment deviation is determined by subtracting an average PQ segment voltage from the ST segment voltage for a heartbeat. The ST deviation provides a measure of the change in variability over a period of time. An ST shift is determined by changes in the ST deviation over a period of time. Deviations of the voltage level of the ST segment may be a result of injury to cardiac muscle, changes in the synchronization of ventricular muscle depolarization, drug or electrolyte influences, and the like. Thus, ST segment variations are a reliable indicator of the possibility of a coronary episode, such as ischemia. ST segment variations indicate a potential coronary episode. Accordingly, at 306, a collection of ST segment variations are determined for a series of cardiac cycles collected over 30 minutes, 60 minutes and the like. Each cardiac cycle has an associated heart rate. When the segment variations are determined, the heart rate is also determined for the particular cardiac cycle.

At 308, multiple heart rate ranges are established. For example, the heart rate ranges may include less than 50 bpm, 50 to 80 bpm, 80 to 100 bpm, 100 to 120 bpm and over 120 bpm. At 308, the segment variations are grouped together based on the associated heart rates of the cardiac signals from which the segment variations were determined. Thus, for example, all segment variations obtained when the patient had a heart rate between 50 and 80 bpm will be grouped in one group associated with the heart rate range 50 to 80 bpm, while all segment variations obtained when the patient had a heart rate between 80 and 100 bpm will be grouped in another group associated with the heart rate range 80 to 100 bpm. The groupings produce distributions associated with different heart rate ranges over a predetermined period of time. By way of example, the distributions may represent histograms. Thus, for example, a histogram would be created showing the distribution of segment variations for the heart rate range 50 to 80 bpm. Similarly, separate histograms would be created showing the distribution of segment variations for each other heart rate range. The segment variations are grouped into histograms to analyze the distributions of segment variations. Optionally, the distributions of segment variations may be grouped and analyzed utilizing other statistical matrixes, such as scatter diagrams, Pareto charts, cause and effect charts, and the like.

At 310, the distributions (e.g., histograms) of segment variations between different heart rate ranges are automatically compared to produce a trending point values (e.g., maximum mean difference) that are associated with a particular collection period of time (e.g., 1 hour). The trending point values over a series of collection periods of time are then grouped to produce trending information (e.g., maximum mean difference over time). For instance, the comparing may automatically identify a relation between the distributions associated with various heart rate ranges during a collection period of time. In one exemplary implementation, one of the distributions of segment variations is identified as a reference distribution. Thus, a first distribution may represent the reference distribution. The reference distribution may be compared to other distributions of segment variations. For example, when the reference distribution corresponds to the lowest heart rate range, the comparison at 310 may compare the distribution of the lowest heart rate range to the distributions associated with the intermediate and high heart rate ranges.

The comparison between the distributions may be based on statistical parameters. The statistical parameters to be compared may include, for instance, a mean, a mode, a variance, an average deviation, a standard deviation, and the like. For example, the comparison may determine a maximum difference in mean between the lowest heart rate range, intermediate and high heart rate ranges. The maximum difference in the statistical parameter between at least two distributions of segment variations is saved as a trending point value at 312.

In accordance with one embodiment, the operations at 304 to 312 are repeated periodically. For example, 304 to 312 may be repeated once every hour, once every four hours, twice per day and the like. Thus, when cardiac signals are obtained at 304 for a one hour period, every four hours, the process 300 repeats 6 times every 24 hour period. As a further example, the period of time at 304 may be 30 minutes and the operations at 304 to 312 may be repeated every 2 hours. Thus, after 24 hours, 12 trending point values would be known. The trending point values may be saved and maintained as separate values or combined (e.g., averaged) to form a single average trending point value for the 24 hour period. Alternatively, 304 to 312 may be repeated continuously, immediately upon the conclusion of each period of time in 304.

After each cycle through operations 304 to 312, at least one new trending point value is obtained. After a collection of cycles through operations 304 to 312 (e.g., 20 weeks, 3 months, 1 year), the trending point values over time form a collection of trend information. For example, the operations at 304 to 312 may be repeated once every 4 hours and the trending point values for a 24 hour period may be averaged. Thus, after a 32 week period, 32 average trending point values would be known. As a further example, each average trending point value may represent an average for a maximum difference in mean segment variation between different heart rate ranges measured over a 24 hour period.

The trending information provides a presentation of values for a statistical parameter over a period of time. For example, the values for the statistical parameter may represent differences in the maximum segment variation between different heart rate ranges over a predetermined period of time. Alternatively, the trending information may include presenting an ST segment variation trend across different heart rate ranges. The process 300 presents the trending information over a predetermined period of time in a desired format. For instance, the trending information may be presented as graphs in scatter diagrams, Pareto charts, cause and effect charts and the like. At 312, the process terminates and may be repeated.

Figure 6A:
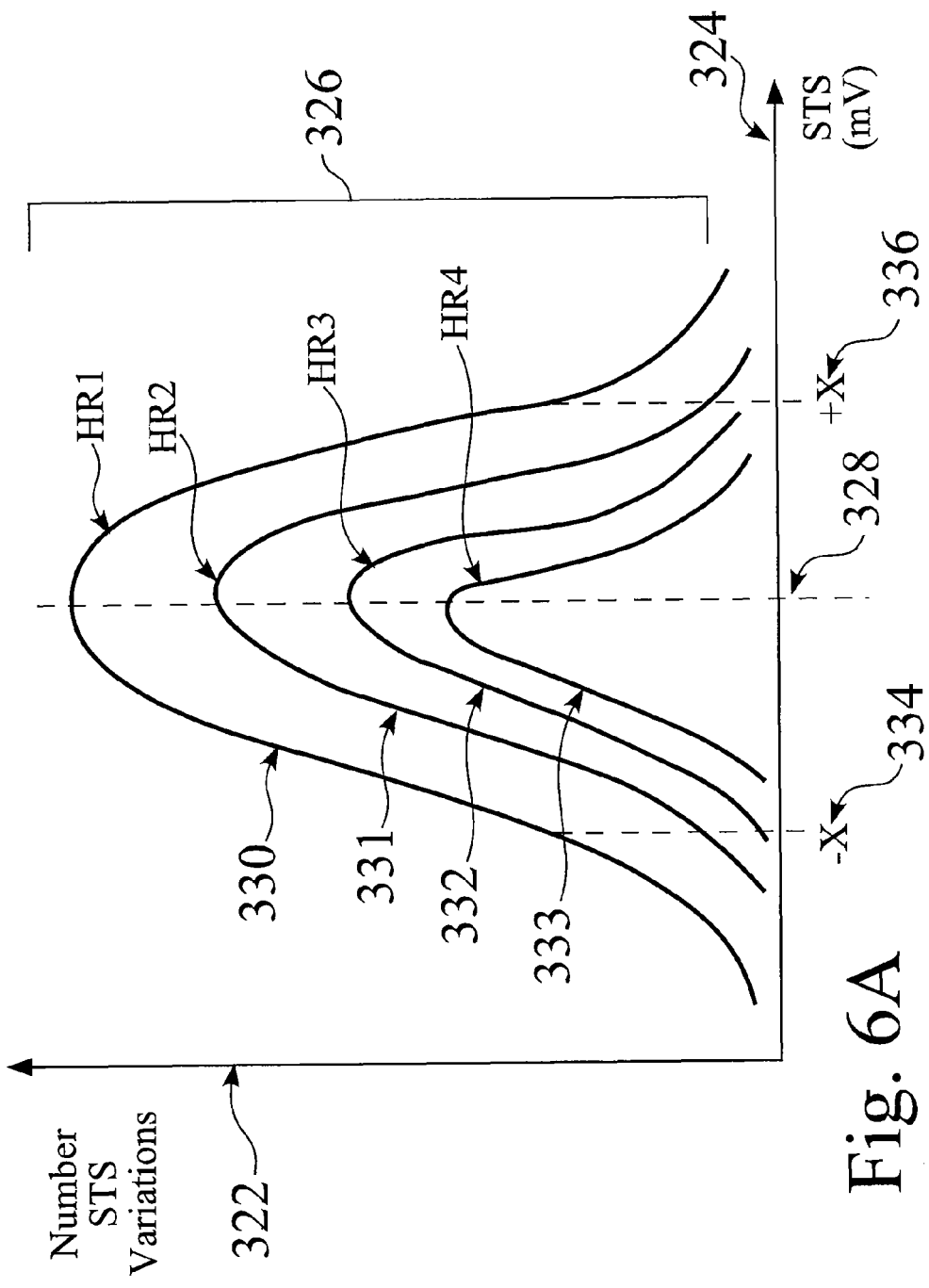
FIG. 6A illustrates a histogram of a healthy person for purposes of better understanding certain embodiments of the present invention.

FIG. 6A illustrates a set of histograms 330-333 for a healthy person that may be collected during one iteration through operations 304 to 312 for purposes of better understanding certain embodiments of the present invention. Histograms 330-333 plot, on the vertical axis 322, the number of ST segment variations that occur during a predetermined collection period of time (e.g., 10 minutes, one hour, a day and the like) and, on the horizontal axis 324, the ST segment variation value in millivolts. The ST segment variations are grouped into heart rate ranges or bins 326 (e.g., HR1, HR2, HR3, HR4 and the like) according to their particular heart rate. Each heart rate bin 326 spans a range of heart rates. For example, HR1 may range from 50 bpm to 80 bpm. HR2 may range from 80-100 bpm. HR3 may range from 100-120 bpm, and HR4 may include heart rates above 120 bpm. The set of histograms 320 is associated with four different heart rate bins 326 (e.g., HR1, HR2, HR3 and HR4) centered about a mode 328. The distribution within each heart rate bin 326 may be characterized by an associated statistical parameter. For example, the mode 328 may represent the statistical parameter of interest. Alternatively, the statistical parameter may represent, for example, an average value, an average deviation, a standard deviation, and the like. When the associated statistical parameter is average or standard deviation it will have a positive value 336 and a negative value 334. Histograms 330-333 are shown that are associated with four different heart rate bins 326 (e.g., HR1, HR2, HR3, and HR 4). Alternatively, more or fewer heart rate bins may be utilized. In general, for a healthy person, the heart rate bins 326 would have closely located or even a common mode, e.g., mode 328.

Figure 6B:
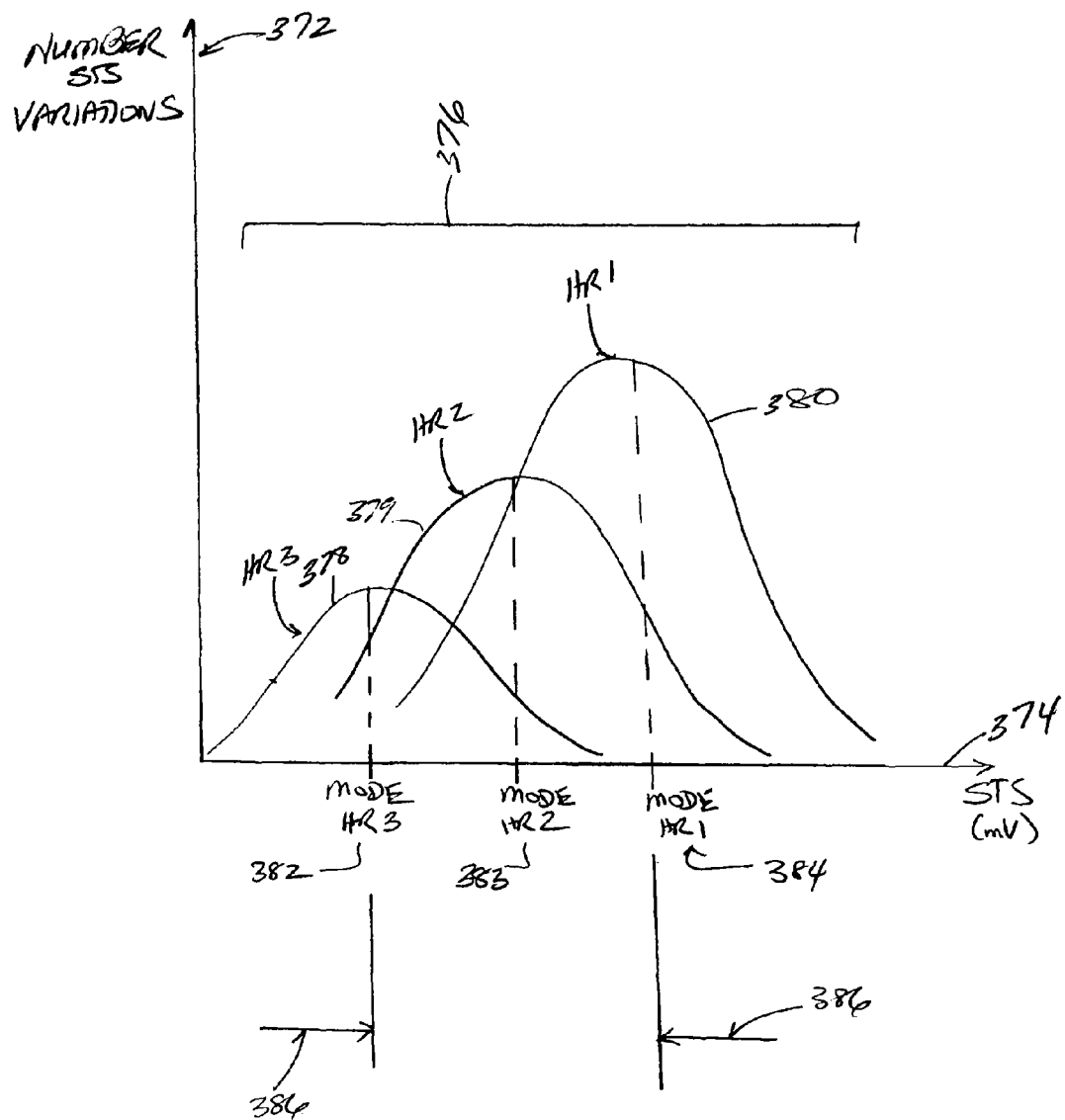
FIG. 6B illustrates a histogram of an unhealthy person for purposes of better understanding certain embodiments of the present invention.

FIG. 6B illustrates a set of histograms 378-380 for an unhealthy person that would be collected during one iteration through the operations 304-312 of FIG. 5. Histograms 378-380 plot, on the vertical axis 372, the number of ST segment variations that occur during the predetermined collection period of time and, on the horizontal axis 374, the ST segment shift value in millivolts. The ST segment variations are grouped into heart rate ranges or bins 376 (e.g., HR1, HR2, HR3, and the like) at 308 (FIG. 5), where each heart rate bin 376 spans a range of heart rates.

Histograms 378-380 have an associated statistical parameter, such as a mode 382-384. The maximum difference 386 between the modes is determined by taking the difference between the lowest mode (e.g., mode 382) and the largest mode (e.g., mode 384). Referring to FIG. 5, the maximum difference 386 is determined at 310 and saved at 312 as a trending point value. The maximum difference 386 may be a good indicator of the severity of the coronary burden with respect to duration and magnitude over a predetermined period of time. The greater the maximum difference 386, the more probable a patient is suffering from demand ischemia. Alternatively, a particular heart rate range (e.g., HR2) may be selected as a reference range. Thus, the mode 383 of the distribution 379 is compared to the other mode values (e.g., mode 382 and mode 384) to determine a plurality of difference values. The maximum difference between the modes of HR1 and HR3 and the reference mode may be identified as the trending point value at 310 (FIG. 5) and saved at 312.

Figure 7:
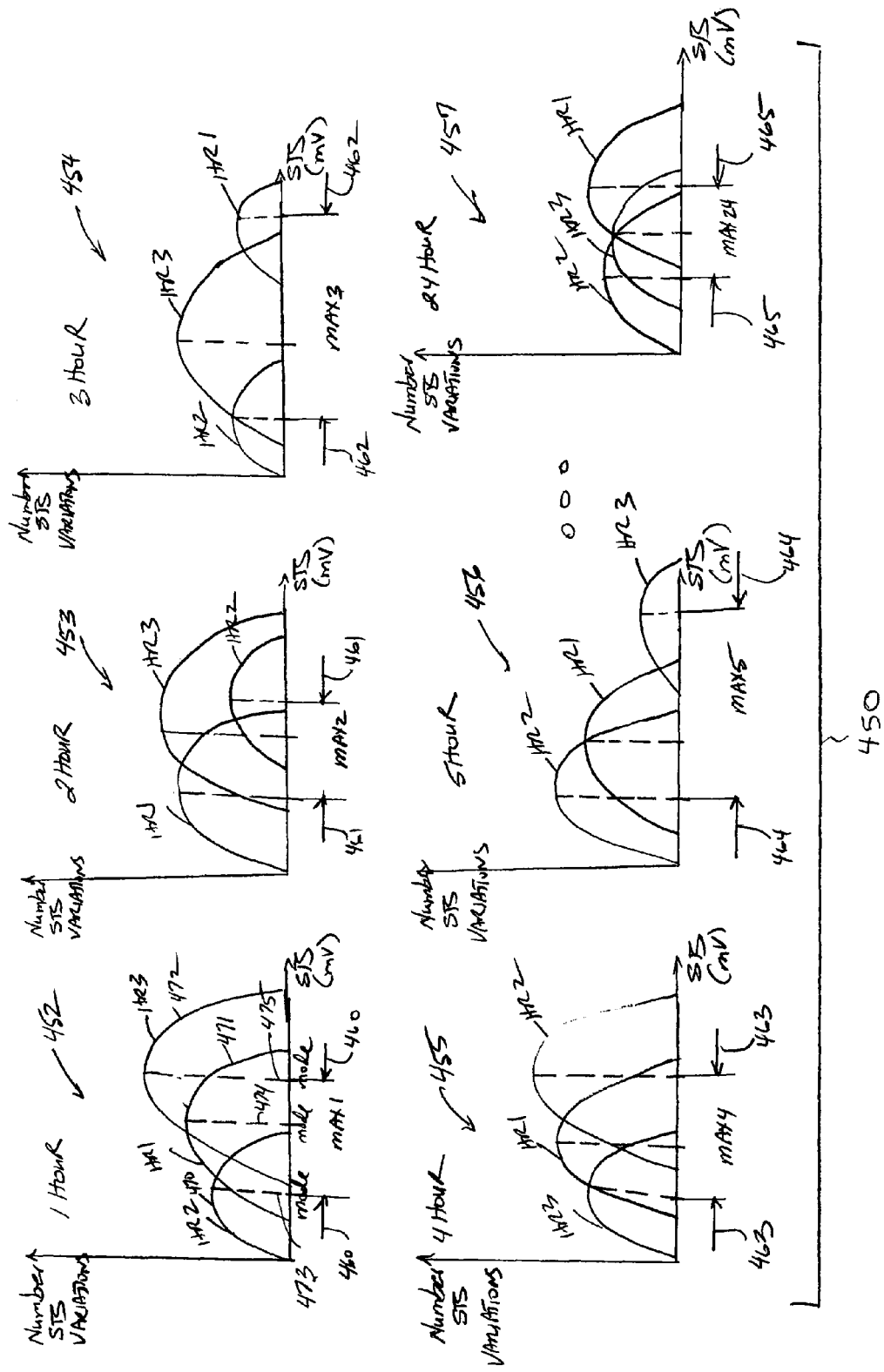
FIG. 7 illustrates a set of histograms recorded over a predetermined period of time utilized in accordance with an embodiment of the present invention.

FIG. 7 illustrates successive sets of histograms 452-457 recorded over a series of iterations through operations 304-312 in accordance with an embodiment of the invention. In the example of FIG. 7, it is assumed that the period of time at 304 for collection one set of histograms is 1 hour. Thus, successive sets of histograms 452-457 may be collected over a twenty-four hour period. Alternatively, the successive sets of histograms 452-457 may be collected for longer periods of time (e.g., forty-eight hours, a week, two weeks, and the like).

The histograms 452-457 are similar to the histograms 378-380 (shown in FIG. 6B) in that each set of histograms 452-457 has associated heart rate ranges or bins. In the example of FIG. 7, each set of histograms 452-457 includes three histograms 470-472 associated with heart rate ranges HR1-HR3. Optionally, the segment variations may be separated into more than three histograms 470-472. For instance, heart rate bins may be established for less than 50 bpm, 50-80 bpm, 80-110 bpm, 110-120 bpm and the like. Each histogram 470-472 has an associated statistical parameter, e.g., mode 473-475. Other statistical parameters may be used, such as an average, a mean, an average deviation, a standard deviation and the like.

During each iteration through 304 to 312 (FIG. 5), a maximum difference 460 to 465 is determined between the modes 473-475 by taking the difference of the ST segment value for the mode having the lowest ST segment value (e.g., mode 473) from the mode having the largest ST segment value (e.g., mode 475). The set of histograms 452 has a maximum mode difference 460; the set of histograms 453 has a maximum mode difference 461. The set of histograms 454 has a maximum mode difference 462. The set of histograms 455 has a maximum mode difference 463. The set of histograms 456 has a maximum mode difference 464. The set of histograms 457 has a maximum mode difference 465. A maximum difference is determined for each set of histograms 452-457. One or more trending point values are saved at 312 (FIG. 5) based on the maximum mode difference values 460-465.

The period of time maybe composed of several intervals of time. For instance, the period of time maybe one day, and for instance, the day maybe composed of multiple intervals, where the intervals are each one hour in duration. Each period of time has one average trending point value. To determine the average trending point value for a predetermined period of time, an average of all the maximum mode values 460-465 over the predetermined period of time is calculated. For example, for a one day period of time, twenty-four maximum mode values are used, where one maximum mode value is determined for each hour interval of time. The resulting average trending point value, e.g., average value for the mode, maybe used as an indicator of ST shift variance for the interval. Once an average trending point value is obtained based on the set of histograms 452-457, the process 300 is reset and repeated periodically. The process 300 is repeated several time to collect a sufficient amount of trending information for analysis.

Figure 8:
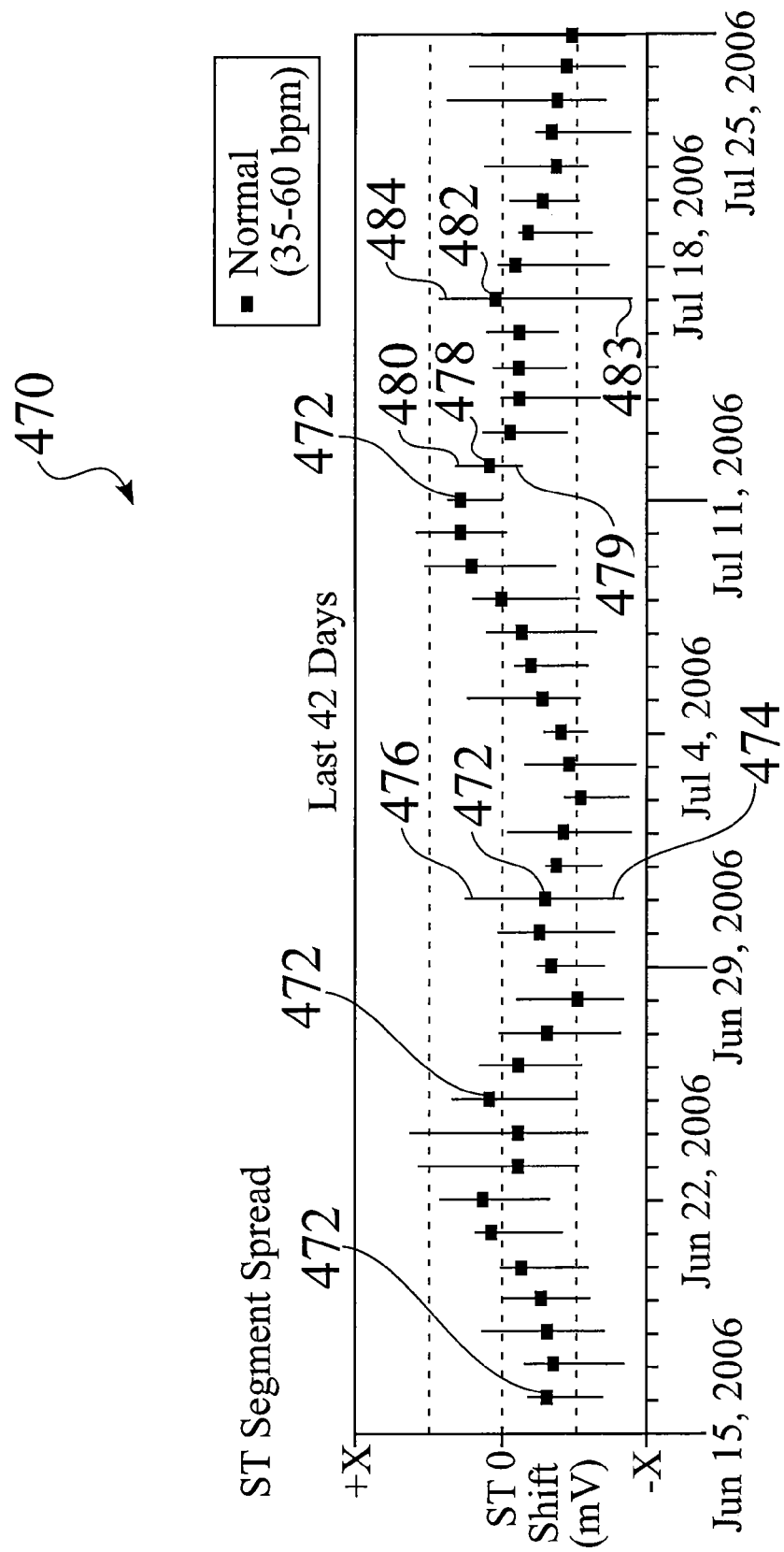
FIG. 8 illustrates a graph depicting a set of trending points in accordance with an embodiment of the present invention.

FIG. 8 illustrates an exemplary graph 470 format for presenting a set of trending point values 472 in accordance with an embodiment of the present invention. The trending point values 472 maybe determined as described above. Each trending point value 472 represents a relation between ST segment variations between heart rate ranges for a predetermined period of time (e.g., one day). Each trending point value 472 is graphed as a candlestick, where the rectangle portion represents the average trending point value such as for a plurality of maximum mode differences over the day. Each candlestick also has an associated lower value 474 and an upper value 476. The lower value 474 represents the lowest maximum mode difference calculated at 310 (FIG. 5) during the twenty-four hour period. The upper value 476 represents the highest maximum mode difference calculated at 310 (FIG. 5) during the twenty-four hour period. Thus, the graph 470 depicts a range of ST segment variation that occurred over a predetermined period of time (e.g., forty-two days) and also shows the range of ST segment values that occurred for a particular day. For instance, trending point 478 shows a lower value 479 and an upper value 480 that are relatively close to one another compared to trending point 482, which shows a lower value 483 and an upper value 484 that are farther apart.

Figure 9:
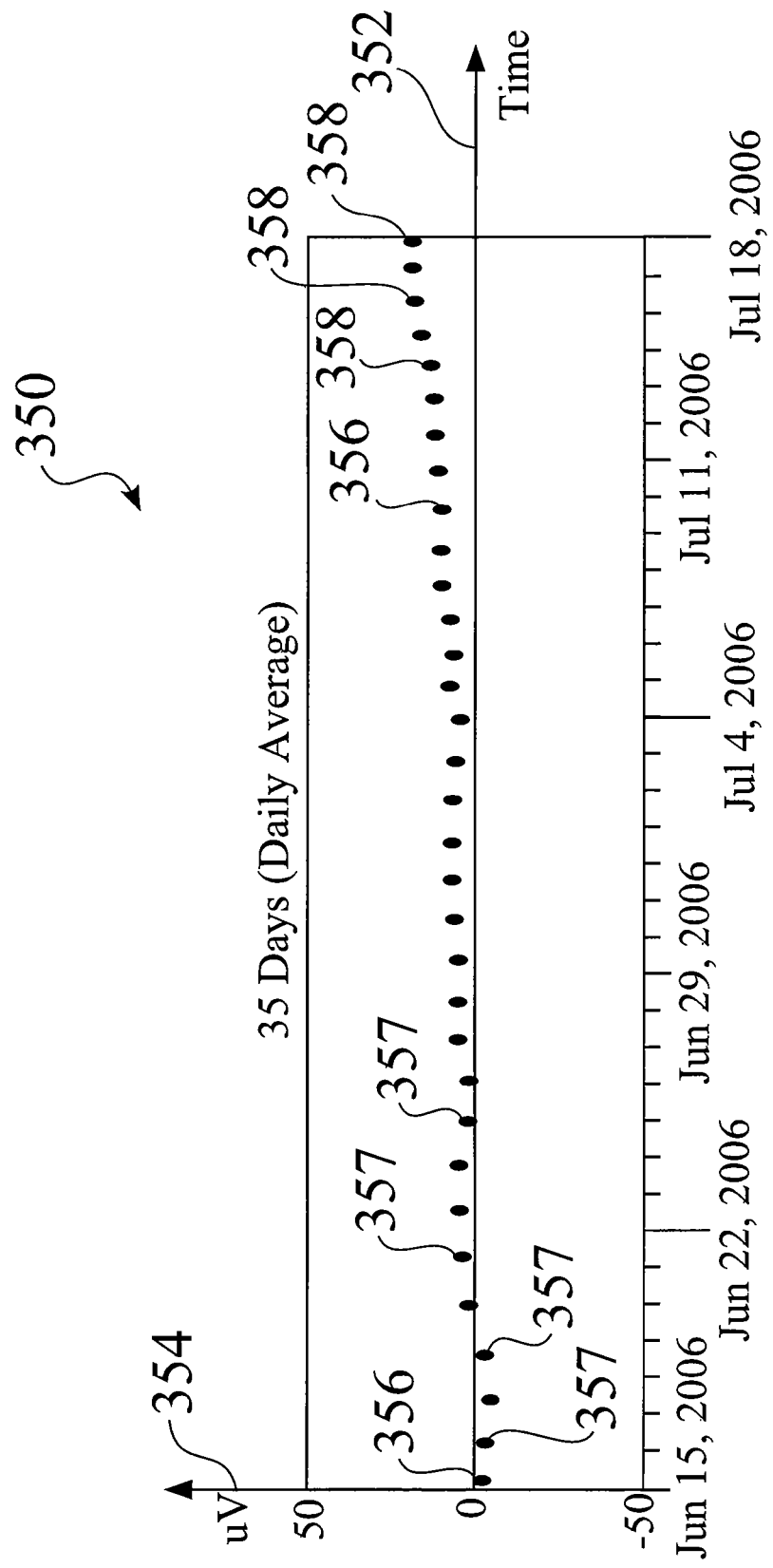
FIG. 9 illustrates a graph depicting a series of trending points over a predetermined period of time that indicate a potential demand ischemia in accordance with an embodiment of the present invention.

FIG. 9 illustrates a graph 350 depicting a different format for presenting a series of trending points 356 over a predetermined period of time. Graph 350 plots, on the horizontal axis 352, time (e.g., in days) and plots, on the vertical axis 354, a ST segment shift value. Any deviations from zero for the trending point indicate a ST segment shift value that potentially indicates a potential coronary episode, such as ischemia. As the deviation from zero increases there is a greater possibility of an ischemic episode. Graph 350 shows that over a predetermined period of time, the trending points 356 may spread from zero. As shown the predetermined period of time is thirty-five days, however any long-term period of time may be used, (e.g., twenty days, thirty days, forty days, sixty days, six months and the like). Trending point values 357 that are close to zero indicate a potential coronary condition but not an ischemia per se. However trending point values 358 indicate a potential demand ischemia. Over a longer period of time (e.g., thirty days), a physician is able to see a rise in the deviation from zero of the trending points; whereas in a smaller period of time (e.g., ten days) very little deviation may occur. The subsequent larger deviation from zero over a long period of time may indicate a serious coronary condition, such as demand ischemia or supply ischemia.

Figure 10:
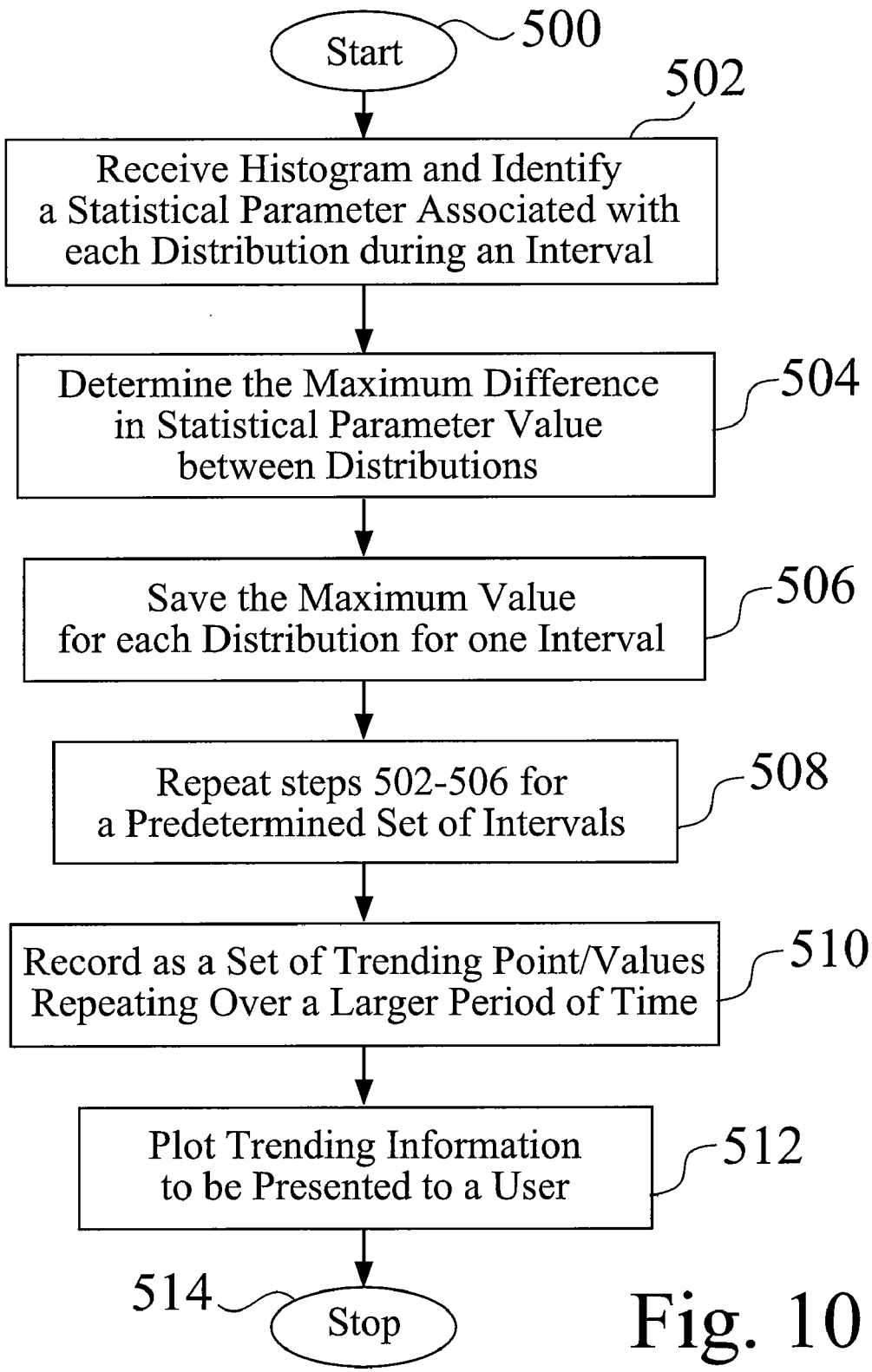
FIG. 10 illustrates a flowchart that depicts a process for plotting trending information in accordance with an embodiment of the present invention.

FIG. 10 illustrates a flowchart that may be implemented by an IMD, a programmer or a workstation based upon previously obtained pre-recorded histograms in accordance with an embodiment of the present invention. At 500 the process begins.

At 502, a series of histogram are retrieved from memory 94 and processor 60 selects a statistical parameter to determine for each histogram. The statistical parameter may be a mode, an average, an average deviation, a standard deviation and the like. Each histogram is associated with a heart rate range. For each heart rate range, a statistical parameter is determined, e.g., mode. At 504, a maximum difference between the statistical parameter values between the histograms is determined. For instance, FIG. 6B shows the maximum difference for a mode value 386 between histograms 378 and 380. At 506 the maximum difference value is stored in memory 94.

At 508, steps 502 through 506 are repeated for each set of histograms that have been saved in memory 94 over a predetermined period of time. Each set of histograms is associated with an interval of time that occurs during a longer predetermined period of time. For instance, a predetermined period of time maybe a day, wherein an interval of time within the day may be an hour. Thus, twenty-four sets of histograms may be stored, each histogram in each set having a maximum difference mode value. Alternatively, the predetermined period of time may be longer, e.g., a few days, a week, a month and the like. Optionally, the interval of time may be longer or shorter, e.g., one-half hour, two hours, four hours, six hours, and the like. At 510, a trending point value is determined for each predetermined period of time based on an average of the maximum difference values for each histogram for each interval of time. Therefore, an average of the twenty-four maximum difference values representing each hour in a day is determined to represent a trending point value for the day. The trending point value is saved in memory 94.

At 512, for each day, a trending point value is determined and plotted on a graph. Over a predetermined period of time, e.g., a month, the trending point values may show gradual deviations from a zero value (shown in FIGS. 8 and 9) that indicates a potential coronary condition. At 514, the process terminates and may be repeated.

Figure 11A:
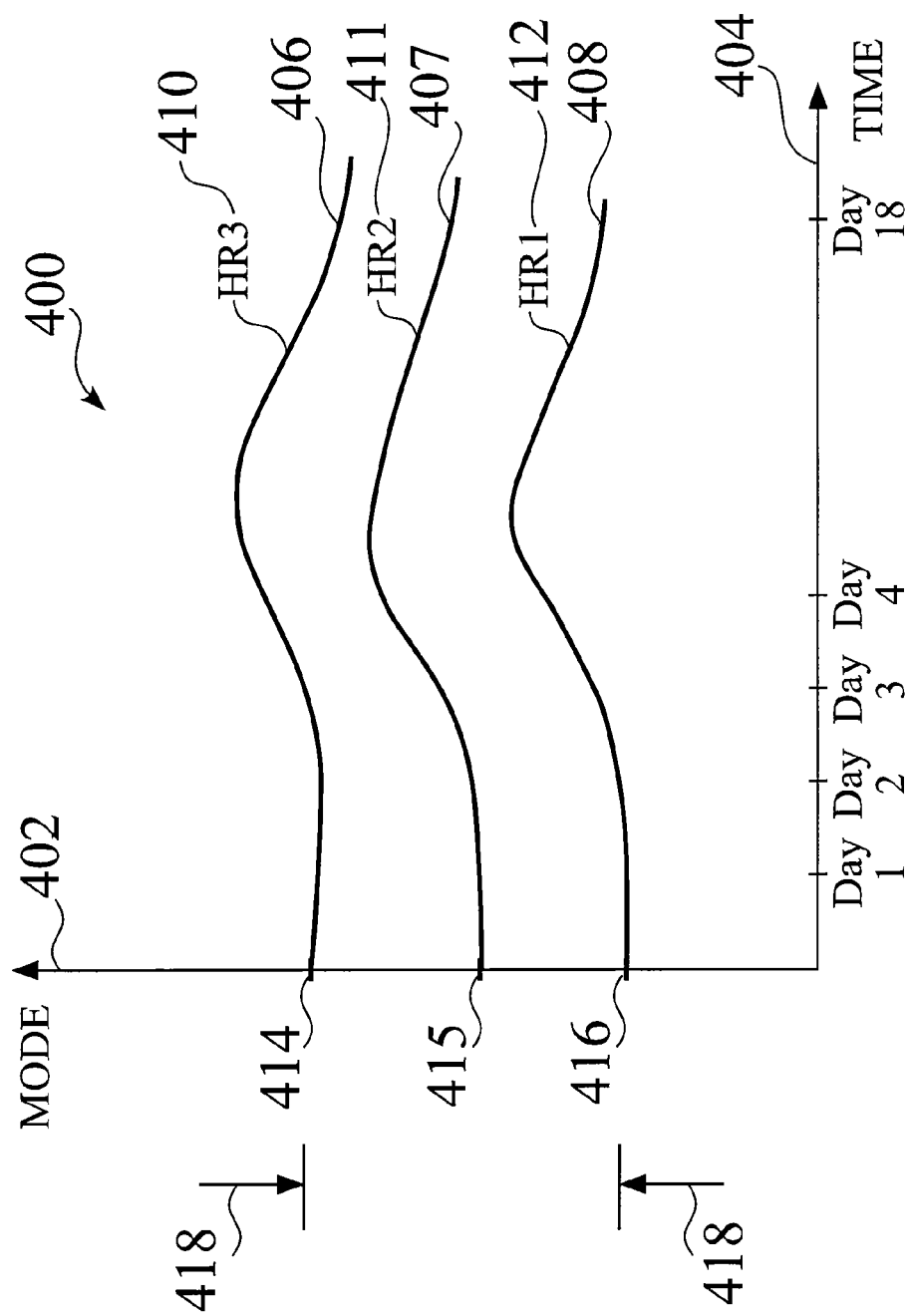
FIG. 11A illustrates a graph showing trend data presented over time in accordance with an embodiment of the present invention.

FIG. 11A illustrates an alternative format for presenting trending information in accordance with an embodiment of the present invention. The trend data 400 plots, on the vertical axis 402, the mode, and on the horizontal axis 404, time (e.g., in days). The mode represents an average of all the mode values for each histogram that occurred on a particular day. Each trending curve 406-408 represents an ST segment variation trend across an associated heart rate range. For instance, trending curve 406 represents a set of average mode values that occurred for a heart rate bin 410 (e.g., HR3) over a predetermined period of time (e.g., eighteen days). Similarly, trending curve 407 represents a set of average mode values that occurred for a heart rate bin 411 (e.g., HR 2) over a predetermined period of time, and trending curve 408 represents a set of average mode values that occurred for a heart rate bin 412 (e.g., HR 1) over a predetermined period of time. Other predetermined periods of time may be used, for example, a week, fourteen days, a month, six weeks, and the like. The trend data 400 allows a physician to compare modes 414-416 across different heart rate ranges 410-412. Differences in the value of modes 414-416 indicates to a physician that a patient may be suffering from a coronary burden (e.g., demand ischemia, supply ischemia) because in a healthy patient there is no change in mode across all heart rate ranges 410-412 (e.g., there is one mode value for all heart rate bins for a healthy patient). The maximum difference 418 between mode 414 and mode 416 indicates the severity of the coronary burden and the greater the difference indicates the more probable a patient is suffering from demand ischemia.

FIG. 11B illustrates an alternative format for presenting trend data 430 to indicate the number of heart beats or samples in each heart rate range for a given time period in accordance with an embodiment of the present invention. Trend data 430 is similar to trend data 400 (shown in FIG. 11A). The trend data 430 plots, on the vertical axis 432, the mode, and on the horizontal axis 434, time (e.g., in days). Trend data 430 shows, as an example, one histogram 411 (e.g. HR2) from the trend data 400 (shown in FIG. 11A). The number of heart beats collected per unit time 436 in a given heart rate range is represented by rectangles 436 having varying heights. The greater the height of the rectangle 436, the great the number of heart beats occurred in the heart rate range. For instance, rectangle 436 acquired in the heart rate range during the time period indicates that a greater number of heart beats at time #4 as compared to rectangle 437. As further example, rectangle 437 and 438 indicate that more heart beats occurred in HR2 during time #14, as compared to the number of heart beats during time #17.

Alternatively, the number of heart beats per unit time may be displayed in different colors. Optionally, the number of heart beats may be shown by a thicker or thinner line (e.g., a candlestick), where a thicker line indicates a greater number of heartbeats per unit time, and a thinner line indicates fewer heartbeats per unit time. The number of heart beats per unit time 436-438 associated with a particular histogram 411 (e.g., HR2), indicates the number of heart beats to produce the average value for the mode 432. Further, the number of heart beats per unit time 436-438 allow a physician to weight a particular histogram 411 compared to other histograms (shown in FIG. 11A).

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

While the invention has been described in terms of various specific embodiments, those skilled in the art will recognize that the invention can be practiced with modification within the spirit and scope of the claims.

What is claimed is:

1. A method for trending variation in coronary burden across multiple heart rate ranges, comprising:
   obtaining cardiac signals over multiple collection time periods within a trending period of time, each cardiac signal having an associated heart rate falling within at least one of the heart rate ranges, each cardiac signal having a segment of interest;
   determining segment variations of the segment of interest within the cardiac signals;
   for each collection time period, grouping the segment variations based on the associated heart rates of the cardiac signals from which the segment variations were determined to produce a set of distributions of segment variations, each of the distributions being uniquely associated with one of the heart rate ranges;
   within each set of distributions, comparing automatically the distributions of segment variations, between different heart rate ranges, to produce trending information representing a relation between the distributions within the corresponding set of distributions and for the corresponding collection time period; and
   presenting the trending information for the multiple collection time periods over the trending period of time.

2. The method of claim 1, wherein the relation includes differences in distributions between different heart rate ranges over the trending period of time.

3. The method of claim 1, wherein the presenting further comprises graphing the trending information over the trending period of time.

4. The method of claim 1, wherein the segment variations represent ST segment variations, the presenting operation further comprising presenting ST segment variations as the trending information over the trending period of time.

5. The method of claim 1, wherein the segment variations represent ST segment variations and the distributions represent histograms of the ST segment variations over the corresponding collection time periods.

6. The method of claim 1, wherein the grouping produces a first set of distributions obtained during a first collection time period and produces a second set of distributions obtained during a second collection time period, the comparing automatically identifying a relation between the first and second sets of distributions.

7. The method of claim 1, wherein the segment variation represents one of ST segment shift and ST segment deviation.

8. The method of claim 1, further comprising, within each set of distributions, identifying one of the distributions of segment variations having a maximum value of a statistical parameter of interest, the comparing being performed relative to the maximum value.

9. The method of claim 1, further comprising, within each set of distributions, identifying one of the distributions of segment variations as a reference distribution, the comparing including comparing the reference distribution to at least one other of the distributions of segment variations.

10. The method of claim 1, further comprising analyzing, for each of the distributions of segment variation, at least one of mean, mode, variance, average deviation and standard deviation to obtain a statistical parameter, the comparing being based on the statistical parameter.

11. The method of claim 1, wherein the comparing determines a difference between at least one of mean, mode, variance, average deviation and standard deviation for the corresponding set of distributions of segment variations.

12. The method of claim 1, wherein the distribution of segment variation represents a histogram.

13. The method of claim 1, wherein the segment variation represents ST segment variation, the distributions of segment variations represent histograms and the comparing includes determining a difference in values for a parameter associated with the histograms across different heart rate ranges over a each of the collection time periods.

14. The method of claim 1, wherein the grouping includes repeatedly grouping multiple first sets and multiple second sets of distributions and the comparing produces multiple corresponding relations as trending points over the trending period of time.

15. A system for trending variation in coronary burden across multiple heart rate ranges, comprising:
   an input for obtaining cardiac signals over multiple collection time periods within a trending period of time, each cardiac signal having an associated heart rate falling within at least one of the heart rate ranges, each cardiac signal having a segment of interest;
   a processor for determining segment variations of the segment of interest within the cardiac signals, the processor for each collection time period, grouping the segment variations, for each collection time period, based on the associated heart rates of the cardiac signals from which the segment variations were determined to produce a set of distributions of segment variations for each collection time period, each of the distributions being uniquely associated with one of the heart rate ranges; and
   memory storing the sets of distributions, within each set of distributions, the processor comparing the distributions of segment variations within each set of distributions, to produce trending information that represents a relation between the distributions within the corresponding set of distributions and for the corresponding collection time period, the memory storing the trending information for the multiple collection time periods over the trending period of time.

16. The system of claim 15, wherein the relations identified by the processor represent differences in distributions between different heart rate ranges over the trending period of time, the differences defining the trending information.

17. The system of claim 15, further comprising means for graphing the trending information over the trending period of time.

18. The system of claim 15, further comprising a display presenting the trending information over the trending period of time.

19. The system of claim 15, wherein the memory stores a first set of distributions obtained during a first collection time period and stores a second set of distributions obtained during a second collection time period, the processor identifying the relation between the first and second sets of distributions.

20. The system of claim 15, wherein the distributions of segment variations include first and second distributions that are characterized by first and second values for a statistical parameter, the processor determining a difference between first and second values for the statistical parameter.

21. The system of claim 15, wherein the memory stores the distributions of segment variations as histograms, each of the histograms being associated with a different heart rate range.

22. The system of claim 15, wherein the segment variation represents ST segment variation, the memory storing the distributions as histograms associated with different heart rate ranges, the processor determining differences between the histograms of heart rate ranges over each of the collection time periods.

23. The system of claim 15, wherein the memory repeatedly stores multiple first sets and multiple second sets of distributions and the processor identifies multiple corresponding relations as trending points over the trending period of time.

* * * * *